US008894749B2

(12) United States Patent
Jonsson et al.

(10) Patent No.: US 8,894,749 B2
(45) Date of Patent: Nov. 25, 2014

(54) BUBBLE REDUCER FOR ELIMINATING GAS BUBBLES FROM A FLOW

(75) Inventors: Per Jonsson, Umeå (SE); Bernd Stegmayr, Umeå (SE); Ulf Forsberg, Skellefteå (SE); Christofer Stegmayr, Nacka (SE)

(73) Assignee: Embody AB (SE)

( * ) Notice: Subject to any disclaimer, the term of this patent is extended or adjusted under 35 U.S.C. 154(b) by 389 days.

(21) Appl. No.: 13/381,569

(22) PCT Filed: Jul. 2, 2010

(86) PCT No.: PCT/SE2010/050764
§ 371 (c)(1),
(2), (4) Date: Apr. 23, 2012

(87) PCT Pub. No.: WO2011/002410
PCT Pub. Date: Jan. 6, 2011

(65) Prior Publication Data
US 2012/0216679 A1    Aug. 30, 2012

Related U.S. Application Data

(60) Provisional application No. 61/233,152, filed on Aug. 12, 2009.

(30) Foreign Application Priority Data

Jul. 3, 2009  (SE) ..................................... 0950521

(51) Int. Cl.
*B01D 19/00* (2006.01)
*A61M 1/36* (2006.01)

(52) U.S. Cl.
CPC .......... *A61M 1/3627* (2013.01); *B01D 19/0042* (2013.01)
USPC .................................. 95/260; 96/194; 96/204

(58) Field of Classification Search
CPC .................... B01D 19/0042; A61M 1/3627
USPC ...................................... 95/260; 96/194, 204
See application file for complete search history.

(56) References Cited

U.S. PATENT DOCUMENTS

| 4,493,705 A | * | 1/1985 | Gordon et al. ................ 604/122 |
| 4,863,452 A | | 9/1989 | Rmiter et al. |

(Continued)

FOREIGN PATENT DOCUMENTS

| GB | 451905 A | 8/1936 |
| WO | WO-2006/030263 A1 | 3/2006 |

OTHER PUBLICATIONS

"International Application Serial No. PCT/SE2010/050764, International Preliminary Report on Patentability mailed Jan. 12, 2012", 9 pgs.

(Continued)

*Primary Examiner* — Duane Smith
*Assistant Examiner* — Douglas Theisen
(74) *Attorney, Agent, or Firm* — Schwegman Lundberg & Woessner, P.A.

(57) ABSTRACT

A microbubble reducer for eliminating and/or removing bubbles of gas from a flow comprising non-Newtonian fluids, wherein the microbubble reducer comprises an inlet at a low point, a curved duct means comprising a gas outlet at a high point, an outlet at a low point, and a lumen that runs through said inlet, said curved duct means, said gas outlet, and said outlet. Additionally, including various methods for removing gas from a flow comprising non-Newtonian fluid(s) using the microbubble reducer, an apparatus comprising the microbubble reducer, and uses of the microbubble reducer pertaining to dialysis or similar treatments, inter alia hemodialysis, plasma exchange, for infusion of blood and other non-Newtonian fluids, and in a heart-lung machine.

19 Claims, 11 Drawing Sheets

(56) References Cited

U.S. PATENT DOCUMENTS

| | | | |
|---|---|---|---|
| 5,061,236 A | 10/1991 | Sutherland et al. | |
| 5,228,889 A * | 7/1993 | Cortial et al. | 96/157 |
| 2007/0045188 A1 | 3/2007 | Blanton | |

OTHER PUBLICATIONS

Jonsson, P., et al., "Air Bubbles Pass the Security System of the Dialysis Device Without Alarming", *Artificial Organs*, 31(2), (2007), 132-139.

Polaschegg, H.-D., "Letter to the Editior—Hemodialysis Machine Air Detectors Need Not Detect Microbubbles", *Artifical Organs*, 31(12), (2007), 911-912.

"International Application Serial No. PCT/SE2010/050764, International Search Report mailed Sep. 20, 2010", 4 pgs.

"International Application Serial No. PCT/SE2010/050764, Written Opinion mailed Sep. 20, 2010", 7 pgs.

Forsberg, U., et al., "Microemboli, developed during haemodialysis, pass the lung barrier and may cause ischaemiclesions in organs such as the brain", *Nephrol. Dial Transplant*, 25, (2010), 2691-2695.

\* cited by examiner

BUBBLE REDUCER FOR ELIMINATING GAS BUBBLES FROM A FLOW

RELATED APPLICATIONS

This application is a nationalization under 35 U.S.C. 371 of PCT/SE2010/050764, filed Jul. 2, 2010 and published as WO 2011/002410 A1 on Jan. 6, 2011, which claims priority to Sweden Patent Application No. 0950521-5, filed Jul. 3, 2009; and to U.S. Provisional Application Ser. No. 61/233,152, filed Aug. 12, 2009; which applications and publication are incorporated herein by reference in their entirety.

TECHNICAL FIELD

The present invention relates to a device for eliminating bubbles of gas from a flow comprising non-Newtonian fluid(s), as well as use, methods, and apparatuses relating to said device. Specifically, the invention relates to air removal in extracorporeal circulation, for instance in dialysis, or infusion therapy with flow infused in venous blood.

TECHNICAL BACKGROUND

Inadequate kidney function can be an implication of various diseases, disorders, and trauma situations, and millions of people worldwide rely on renal replacement therapy for their survival. Dialysis, either through the peritoneal membrane or from the blood (i. e. hemodialysis) is a critical tool in the treatment of patients presenting with acute renal failure, but the technique is equally important for maintenance treatment of patients with chronic kidney diseases of various types and origins. Indications necessitating dialysis include inter alia severe retention of products not wasted by impaired kidneys, for instance urea, creatinine, uric acid, potassium, and phosphate, but also fluid overload, or even acute drug poisoning, to name a few.

Hemodialysis can be carried out either as an outpatient or as an inpatient therapy, but careful monitoring and surveillance is nevertheless pivotal irrespective of the situation, as numerous side effects and complications, both immediate and long-term, are associated with the procedure. These effects are sometimes dictated by the different types of hemodialysis access methods utilized, but the dialysis procedure per se is also associated with certain inherent risks, normally requiring both staff surveillance and automatic monitoring.

Hemodialysis is performed using two separate circuit systems, one circuit carrying the blood from the patient and another carrying dialysis fluid, a solution comprising mineral ions, for removal of waste substances, as well as water, from the blood. The principle behind dialysis is diffusion over a semipermeable membrane, i. e. the dialysis filter, which interconnects the two circuit systems. The blood drawn from the patient (either from an arterio-venous access or from a central dialysis catheter) enters an arterial tube and is subsequently, using a blood pump, flushed into a dialysis filter, where waste products are being removed. The cleansed blood is returned to the patient through the venous part of the tubing. However, despite being a substantially closed circuit, air is constantly leaking in to the blood flow, either as a result of leakage at the watertight connection sites, or as an implication of air present in the circuit prior to starting the dialysis.

As a result of the potentially detrimental effects of air entering the blood stream and subsequently the body, the blood circuit system is carefully monitored through the use of infrared and/or ultrasound safety control systems. The risks associated with entry of large air bubbles into the blood stream has been a long-standing concern within the dialysis field, as a resultant emboli could potentially be lethal to the patient undergoing the renal replacement therapy. Hence, substantial research efforts have been directed towards improving detectors for dialysis monitoring and surveillance, as well as towards developing various types of devices for air removal within the system. An important factor behind the development of systems for improved air removal is the consensus within the research community with regards to the importance of bubble size and the leakage of air as a function of time (Polaschegg, Artificial Organs, 31, 911-912, 2007). The apparent insignificance of microbubbles, i. e. bubbles exhibiting sizes around 100 µm, has been attributed to the collapse and subsequent blood absorption of small bubbles. Additionally, the lungs are considered to function as barriers for bubbles with diameters above 20 µm, and this paradigm, together with the perceived practical impossibility of preventing microbubble entry, today dictates the industry standards.

The venous part of the dialysis system is normally arranged with a venous chamber enabling removal of larger amounts of air present within the system, but such a chamber is only effective in separating bubbles of a relatively large size. As a result of the industry standpoint with regards to microbubbles, these types of air removal systems have been deemed adequate for clinical use. Nevertheless, there is substantial clinical evidence for air emboli passing the venous chamber, which is meant to act as an air trap for larger air bubbles, without activating the alarm (Jonsson, P., et al., "Air bubbles pass the security system of the dialysis device without alarming", *Artif Organs*, (2007), 31(2): 132-9). Extensive data collected by the inventors of the present invention show that these microbubbles pass into the vessels of the patient (Forsberg, U., et al., "Microemboli, developed during haemodialysis, pass the lung barrier and may cause ischaemic lesions in organs such as the brain", *Nephrol Dial Transplant*, (2010), Epub ahead of print), and that the presence of these emboli increase significantly within the arterial system, including the carotid artery (i. e. the main artery for supply to the brain), after start of the dialysis.

Besides an increased incidence of pulmonary damage by venous emboli, arterial microemboli contribute to the increased prevalence of cerebral atrophy and regression of neurocognitive status, especially in long-term dialysis patients, indicating a significant need for improved devices for separation of microbubbles as well as larger bubbles of air.

Venous chambers constituting the current art are normally arranged as vertical drip chambers with the inlet at a high point and the outlet at a low point, in order for large bubbles, i. e. bubbles with a buoyancy force overcoming the drag force from the flow, to ascend vertically upwards. Modified versions include devices designed so as to promote a circulatory flow in the chamber or devices with various types of geometric appearance, for instance substantially cubic shapes.

WO 2006/030263, for instance, discloses a blood chamber for use in an extracorporeal circuit comprising a blood inlet port, a blood containment chamber, and a first conduit. The chamber is arranged with a relatively large segment for slowing down the blood flow and separate gases from the blood, forming an overlying gaseous zone.

As a result of the current paradigm, the venous chambers in the art are constructed to eliminate merely relatively large bubbles, and do not remove microbubbles (i. e. bubbles with sizes under 50-400 µm) at all. Generally, many devices provide very blunt tools for gas separation and numerous devices in fact promote air contamination. Neither are the devices for gas removal specifically adapted to non-Newtonian and relatively viscous fluids such as blood, where elimination of eddies and currents are intrinsically critical. Further, the prior art generally overlook the biological properties of blood, often resulting in coagulation in slow-flowing parts, including filters in connection with stagnant flow or air retention, or corners of the utilized devices, having a negative impact both on the removal of air bubbles but also on the dialysis as such.

Furthermore, devices of the prior art generally exhibit very complex configurations comprising multiple parts, resulting in manufacturing difficulties and an increased risk of air leakage.

SUMMARY OF THE INVENTION

It is thus the object of the present invention to overcome said drawbacks and satisfy existing needs, as well as providing a simple, easily manufactured, and optimized device for efficient separation of gas bubbles, both relatively large bubbles and in particular microbubbles, from an extracorporeal circulation or infusion therapy with flow infused in venous blood. Furthermore, the invention relates to use and methods for removing gas bubbles from a blood flow, as well as apparatuses comprising said device.

More specifically, the present invention relates to a device, i.e. a bubble reducer, for eliminating bubbles of gas from a flow comprising non-Newtonian fluid. The device is capable of reducing bubbles of various sizes but the fact that it has the capacity to eliminate so called microbubbles from a flow comprising non-Newtonian fluid results in significantly improved properties from a clinical perspective. The microbubble reducer may be arranged so that said flow passes not more than one or two other devices prior to entry into a patient, and the microbubble reducer comprises an inlet (10), at a low point, a curved duct means (4), said curved duct means comprising a gas outlet (5) at a high point, an outlet (6) at a low point, and a lumen (21) that runs through said inlet (10), said curved duct means (4), said gas outlet (5), and said outlet (6). The lumen (21) of the microbubble reducer exhibits an increasing cross-sectional area when running through the inlet (10) towards to curved duct means (4), and, further, the lumen (21) of the inlet (10) is arranged with an angle of between −20° and 75° relative a horizontal plane.

The microbubble reducer of the present invention also exhibits a complete lack of any sharp angles, corners, or dead spaces (i.e. spaces substantially without flow velocity). The fact that the device only exhibits smooth transitions between different parts, as well as the absence of corners, sharp angles, and dead spaces, is conducive for obtaining a laminar flow and for eddy reduction, in order to further enhance the gravity-mediated bubble collection and eliminating areas without flow or with low flow, thereby reducing coagulation. In accordance with one embodiment, the running and/or the passage of the lumen (21) through the inlet (10), through the curved duct means (4), through the gas outlet (5), and through the outlet (6) may be described by at least one continuous function without singularities, i.e. the lumen (21) does not have any sharp angles, corners, or dead spaces where the flow becomes slow, or even substantially motionless and/or stationary.

Thus, through the use of exceptionally efficient gas separation, the present invention solves the neglected problem of microbubble elimination, and thereby reducing the significant clinical consequences caused by this disregarded but nevertheless decidedly important phenomenon.

DETAILED DESCRIPTION OF THE INVENTION

The present invention is concerned with a device, e. g. a venous chamber, for eliminating, removing, and/or significantly reducing bubbles of gas, with sizes down to 2.5 μm, from a flow comprising non-Newtonian fluid, a method for removing gas from a flow comprising non-Newtonian fluid, a dialysis apparatus arranged with the microbubble reducer of the invention, as well as the use of the microbubble reducer in removal of gas bubbles from a flow comprising non-Newtonian fluid, in particular for hemodialysis applications.

All words, terms, and abbreviations used in the present application shall be construed as having the meaning usually given to them in the relevant art, unless otherwise indicated. For clarity, some terms are however specifically defined below.

Figure 10:
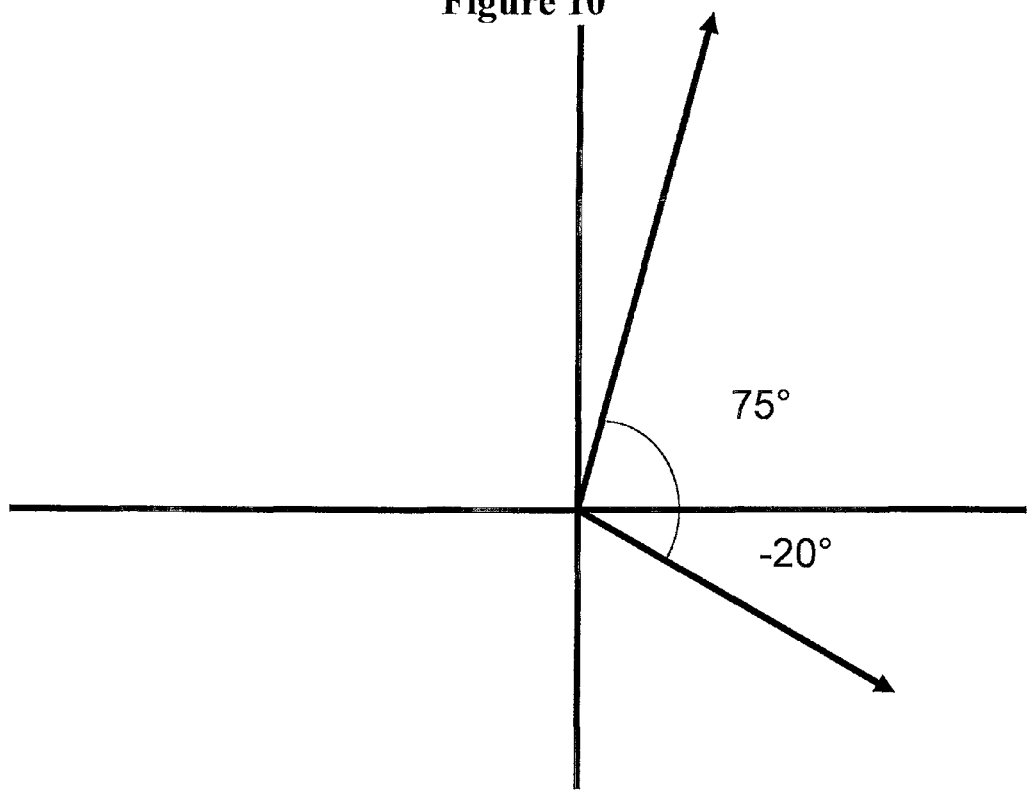
FIG. 10. Graph defining the angular interval utilized for describing the present invention. The arrows indicate the direction of the flow.

The term "lumen" shall be understood to comprise a cavity and/or a hollow and/or a hole with a certain dimensional extension in space and/or a channel and/or a duct. The term "continuous function" shall be recognized as having the meaning usually given to it in the relevant art, i.e. a function which is continuous and differentiable and/or integrable over any interval. The terms "singularity" or "singularity point" shall be understood to pertain to a point where an analytical function is not defined and/or a point where a function is not differentiable (that is, essentially a point where a function stops being well-behaved in some particular way). The terms "singularity" or "singularity point" shall in this particular context be understood to describe corners, sharp angles, and/or dead spaces, meaning that a lumen that may be described by a continuous function without any singularities has substantially only smooth and/or even surfaces and is substantially completely devoid of any corners, sharp angles, and/or dead spaces (i.e. on the inside of the lumen). The term "non-Newtonian fluid" shall be understood to relate to a fluid with a viscosity that changes with changes in the velocity gradient in the fluid (i.e. the shear rate), which in turn depends on the flow velocity. Non-Newtonian fluids may for instance be blood, blood plasma, and blood substitute fluids (artificial blood and/or blood surrogates). The definition of the angles in accordance with the present invention, i.e. the term "from −20° to 75° relative a horizontal plane" shall be understood to relate to the whole interval from −20° to 75°, including 0° (FIG. 10). When said term is utilized in connection with the angle of the inlet (10), the angle of the lumen (21), and/or the angle of the extension channel (30) or the extension channel lumen (41) of the microbubble reducer of the present invention, it shall be understood that said parts may be arranged with an inclination of ≤0°, an inclination of ≥0°, as well as completely/substantially horizontal, that is with an angle substantially equal to 0°. The person skilled in the art naturally immediately recognizes that a horizontal arrangement of the any component of the device is within the scope of the definition of the angular interval. The term "flow passes not more than one or two other devices prior to entry into a patient" is clear and unambiguous for the skilled person and shall be understood to describe that not more than one or two other types of medicine technology devices (for instance a security device, and/or a filter) are placed between the micro bubble reducer of the present invention and a patient that is receiving the flow of non-Newtonian fluid from which the bubbles of gas have been removed, eliminated, and/or reduced using the micro bubble reducer.

As will further be apparent from the description and the examples, the term "curved duct means" relates to a duct displaying a curved shape, preferably a substantially inverted U with curved point placed at the highest point. The terms "air", "gas", "gas bubbles", and "bubbles" shall be understood to relate to undesired gaseous components present in the blood flow. The term "horizontal plane" refers to any plane substantially parallel to the earth plane, the term "low point" refers to the lower part of device, below the high point and substantially below, before, or after the curved duct means, and the term "high point" refers to the higher part of the device, on top of or laterally arranged in relation to the curved duct means. The direction of the flow may be used to define whether an inclination is rising or falling.

One aspect of the present invention is concerned with a device, i.e. a micro bubble reducer, for eliminating bubbles of gas from a flow comprising non-Newtonian fluid, preferably a blood flow. The device is capable of reducing bubbles of various sizes but the fact that it has the capacity to eliminate so called microbubbles from a flow comprising non-Newtonian fluid results in significantly improved properties from a clinical perspective. The microbubble reducer may be arranged so that said flow passes not more than one or two other devices prior to entry into a patient, and the microbubble reducer comprises an inlet (10), at a low point, a curved duct means (4), said curved duct means comprising a gas outlet (5) at a high point, an outlet (6) at a low point, and a lumen (21) that runs through said inlet (10), said curved duct means (4), said gas outlet (5), and said outlet (6). The lumen (21) of the microbubble reducer exhibits an increasing cross-sectional area when running through the inlet (10) towards to curved duct means (4), and, further, the lumen (21) of the inlet (10) is arranged with an angle of between −20° and 75° relative a horizontal plane.

The increasing cross-sectional area along the inlet (10) towards the curve duct means (4) results in a decreased velocity of the blood flow, mediating ascent and thereby separation of gas bubbles present in the flow. At the high point of the curved duct means (4), the separated gas is removed from the device through a gas outlet (5), before the non-Newtonian fluid is conveyed through the outlet (6) further in the venous direction.

The non-Newtonian fluid is introduced into the system through an inlet (10). The inlet (10) is arranged with an angle −20° to 75° relative a horizontal plane (i.e. including 0°, with the purpose of distributing any gas bubbles present in the non-Newtonian fluid to the upper part of the flow. For bubbles displaying small diameters, this is most easily achieved at a high shear rate when the viscosity of the blood is lower. The lumen (21) of the inlet (10) of the present invention has an increasing cross-sectional area in the venous direction, i. e. along the flow, with implications such as decreased flow velocity, fluid decompression, and, upon oversaturation, further upward distribution of the gases and/or gas bubbles present. The length of the inlet (10), and thereby of the lumen (21), can be modified in order to influence the separation of the gas bubbles, e.g. a longer inlet facilitating ascent of gas bubbles. After having passed the inlet, the non-Newtonian flow reaches the curved duct means (4), where gas bubbles are removed through the gas outlet (5), substantially arranged at the high point of the curved duct means (4). The upper part of the device, i.e. the curved duct means (4), enables bubble fusion, creating larger bubbles for facilitated removal through the gas outlet (5). The gas outlet (5) can be constructed in numerous ways, according to the preferred embodiments of the skilled person. Subsequently, the non-Newtonian fluid, with potentially hazardous gas bubbles removed, returns to the patient through the outlet (6). Taken together, the physical characteristics of the device mediate separation of both relatively large bubbles and microbubbles, reducing the risk of adverse events occurring in patients undergoing renal replacement therapies, plasmapheresis and apheresis, hemoperfusion, plasma filtration, or similar techniques (i. e. extracorporeal blood processing with venous infusion), including infusion therapies.

The inclination and the expanding cross-sectional area of the lumen (21) of the inlet (10) results in facilitated bubble ascent, and the absence of corners and angles results in a laminar flow without disturbances. The resultant force between the blood flow and the buoyant force of the gas bubbles constantly directs the bubbles to the upper surface of the tube, except after the curved duct means (4), resulting in a distinct advantage relative devices currently employed within the art.

Numerous parameters affect the flow of non-Newtonian fluids, notably blood, making the dialysis process highly complex and difficult to control. A small cross-sectional area results in a higher flow velocity and a higher shear rate, and, in blood, a lower viscosity. Additionally, water is removed, with varying velocity, during the process, with the implication that the blood being returned to the patient through the venous part of the tubing has an abnormally high erythrocyte concentration, resulting in an anomalously high viscosity. Furthermore, the blood flow is highly variable, depending on factors such as the prescribed treatment and the blood vessel access, adding additional dimensions of complexity to the dialysis process. Hence, optimizing the arrangement and the characteristics of the dialysis tubing is pivotal for efficient air removal and minimized coagulation in fluids of varying viscosity.

The fact that the device is completely devoid of any sharp angles, corners and/or dead space imply significant advantages in terms of reduced disturbance and reduced eddy formation, as well as absence of dead spaces and reduction of slow-flowing fluid, in particular blood, improving separation of bubbles of all sizes, including microbubbles, as well as inhibiting coagulation processes, which are commonly encountered problems associated with numerous other devices for gas separation. Furthermore, the combination of the above features results in a laminar flow for optimized elimination of gas in the non-Newtonian flow. In accordance with one embodiment of the present invention, the running and/or the passage of the lumen (21) through the inlet (10), through the curved duct means (4), through the gas outlet (5), and through the outlet (6) may be described by at least one continuous function without singularities, i.e. the lumen (21) does not have any sharp angles, corners, or dead spaces where the flow becomes slow, or even substantially motionless and/or stationary.

In order to minimize the amount of blood outside the body at any one time during treatment, dialysis devices ought to be as small as possible. Efficient removal of potentially detrimental air in the system is naturally pivotal, wherefore optimized physical properties, in accordance with the present invention, are crucial.

In one embodiment of the invention, the curved duct means (4) is in the form of a substantially inverted U. The U chamber is arranged with exclusively smooth transitions in order to further promote a laminar flow without any disturbances. The tubing component, i.e. the lumen (21) and/or (41) as per below, of the present invention preferably has a substantially circular cross-sectional area, but other geometrical shapes devoid of sharp angles or corners, for instance ovals, are also within the spirit of the invention. For instance, as per the present invention, an oval lumen/tubing (i. e. a lumen/tubing having two different radii) with a vertical radius exceeding its horizontal radius would induce a higher shear rate, a desirable feature at certain blood concentrations. Additionally, in accordance with the invention, the lumen/tubing can display different cross-sectional shapes along for instance the inlet, e. g. an initial oval shape followed by a substantially spherical shape, or vice versa. Furthermore, both different segments displaying different cross-sectional shapes and different shapes together with continuous transitions lie within the scope of the present invention.

Figure 11:
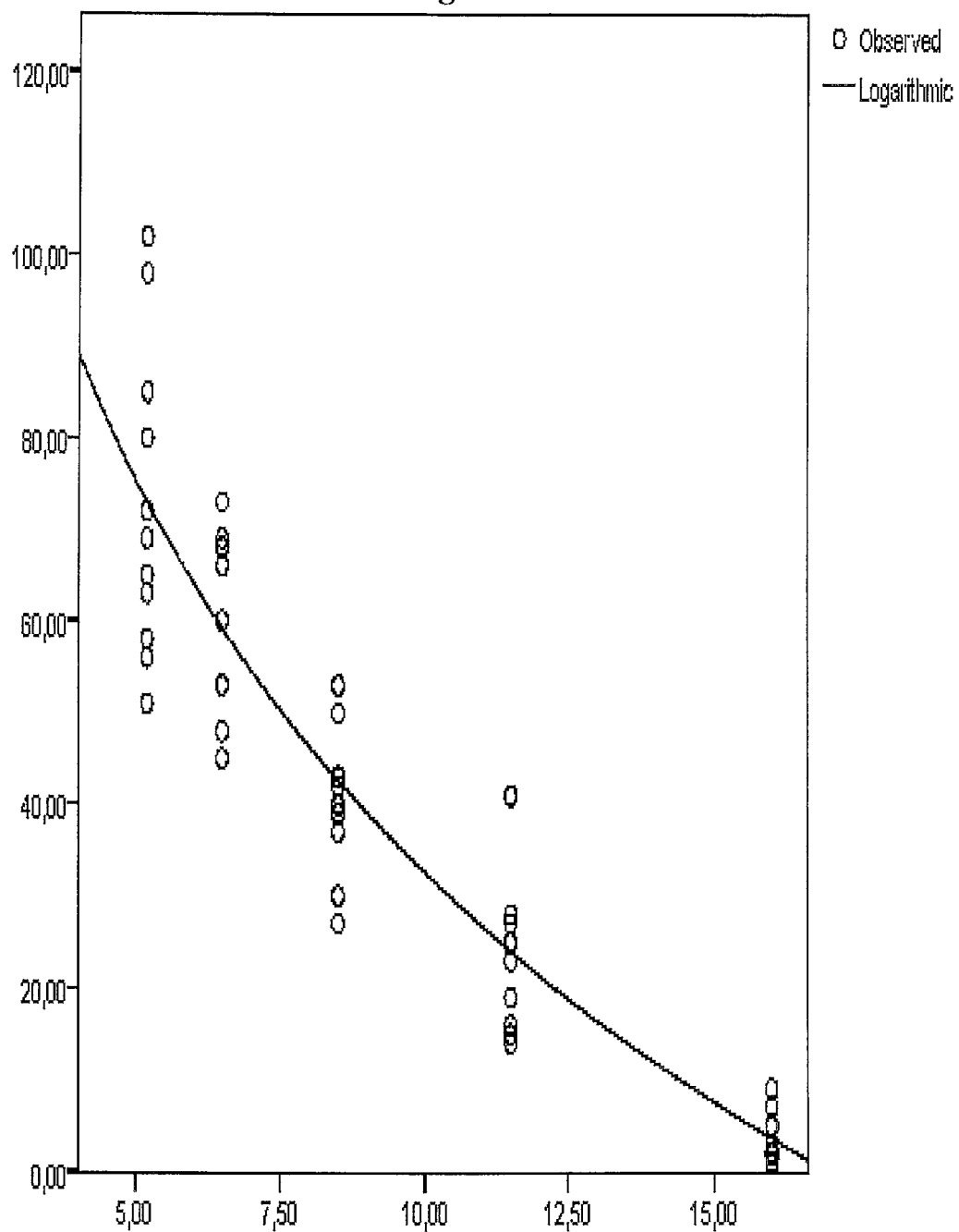
FIG. 11. Graph showing the how the number of bubbles decreases with increasing length of the lumen (21) of the inlet (10). The length designated on the x-axis (i.e. the horizontal axis) refers to the length from the start of lumen (21) to the point where the flow turns downwards towards a horizontal plane, measured along the lower rim of the lumen (21).

As per one embodiment of the present invention, the lumen (21) of the inlet (10) may have a length of at least 2 cm, of at least 3 centimeter, of at least 4 cm, of at least 5 cm, of at least 10 cm, of at least 15 cm, of at least 20 cm, of at least 25 cm, of at least 30 cm, of at least 35 cm, of at least 40 cm, of at least 45 cm, of at least 50 cm, of at least 55 cm, of at least 60 cm, or of at least 1 m. FIG. 11 shows how the bubble removal increased with increasing length of the lumen (21) of the inlet (10), i.e. the longer the lumen (21) the more efficient is the bubble removal/elimination.

Figure 4:
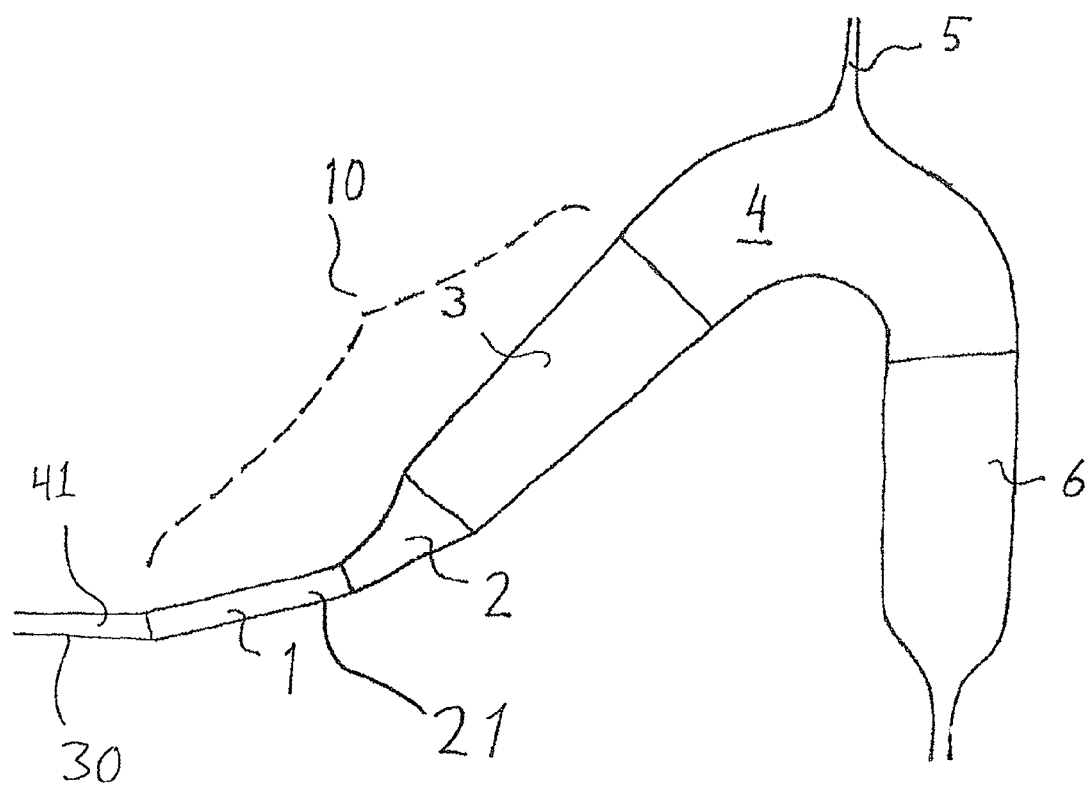
FIG. 4. Schematic exemplary illustration of one embodiment of the present invention, having an inlet (10) with three inclining segments (1, 2, 3) with different cross-sectional areas and with different inclination.
Figure 8:
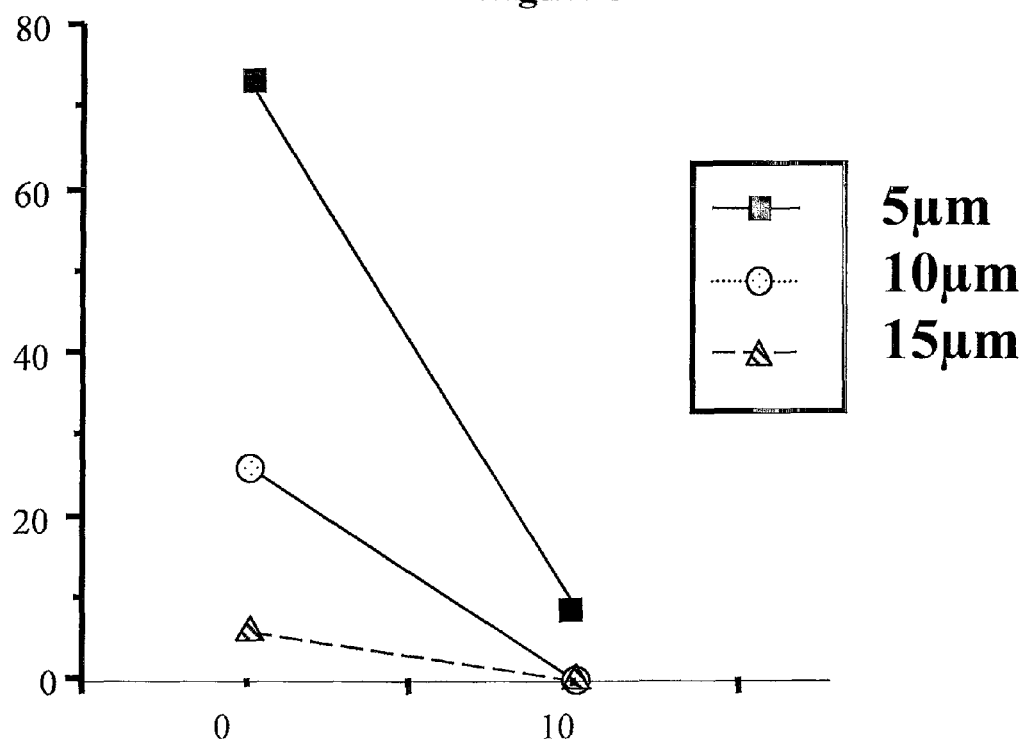
FIG. 8. Graph showing how the length of the extension channel (30) influences the removal and/or elimination of microbubbles. A longer extension channel (30) further enhances the bubble separation and removal.
Figure 9:
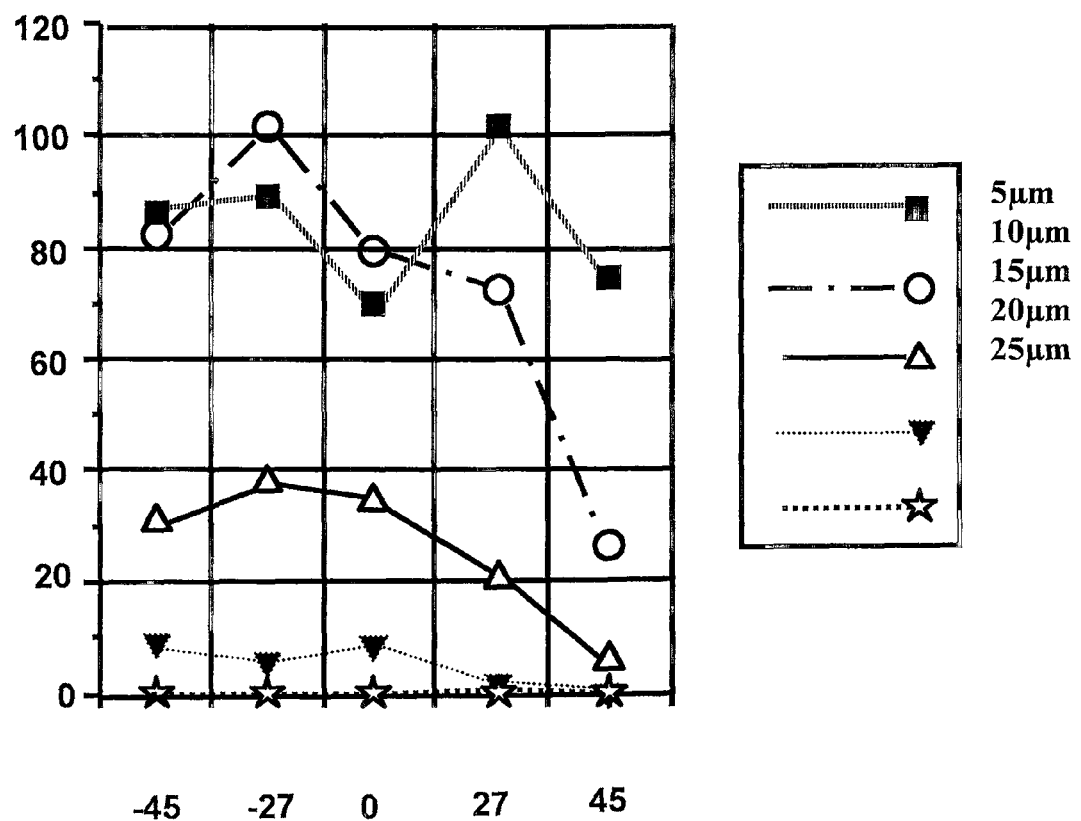
FIG. 9. Graph showing the angle of the inlet (10) influences the removal and/or elimination of microbubbles. An angle of approximately 45° relative a horizontal plane optimizes the bubble separation and removal.

According to a further embodiment of the present invention, the microbubble reducer may further comprise an extension channel (30) comprising a lumen (41), wherein said lumen (41) of said extension channel (30) is arranged to empty into and/or transit into the lumen (21) of the inlet (10) (FIG. 4). The extension channel (30) may have a length of at least 2 cm, of at least 3 centimeter, of at least 4 cm, of at least 5 cm, of at least 10 cm, of at least 15 cm, of at least 20 cm, of at least 25 cm, of at least 30 cm, of at least 35 cm, of at least 40 cm, of at least 45 cm, of at least 50 cm, of at least 55 cm, of at least 60 cm, or of at least 1 m. FIG. 8 clearly illustrates how the length of the extension channel (30) contributes to enhanced removal and/or elimination of bubbles of different sizes.

Further, as per another embodiment of the present invention, the extension channel (30) may be arranged with an angle of between −20° and 75° relative a horizontal plane, that is including 0° (the extension channel (30) may thus be horizontally arranged), in order to distribute the gas bubbles along the upper part of the flow.

In accordance with yet another embodiment, the distance from the start of the inlet (10) to the highest point of the lumen (21) of the curved duct means (4) may be at least 3 centimeter, of at least 4 cm, of at least 5 cm, of at least 10 cm, of at least 15 cm, of at least 20 cm, of at least 25 cm, of at least 30 cm, of at least 35 cm, of at least 40 cm, of at least 45 cm, of at least 50 cm, of at least 55 cm, of at least 60 cm, or of at least 1 m. The distance from the start of the inlet (10) to the highest point of the lumen (21) of the curved duct means (4) shall be understood to relate to the distance from a central point in a cross-section of the lumen (21) at the start of the inlet (10) to the highest point of the lumen (21) of the curved duct means (4).

According to a further embodiment, the inlet may have an angle of between 0° to 75° relative a horizontal plane, preferably between 35° and 55°, and most preferably approximately 45° relative a horizontal plane, in order to avoid bubble adherence and instead facilitate upward bubble migration in the microbubble reducer (i. e. to promote removal of gas bubbles and to avoid re-mixing of gas bubbles that have ascended to the top into the fluid). Additionally, the inlet (10) may display increasing cross-sectional area towards the curved duct means, either arranged so as to increase in a segment-by-segment (1, 2, and 3 in FIGS. 2-5) fashion or through continuous expansion (FIG. 1).

The increasing cross-sectional area of the lumen (21) of the inlet (10) results, as abovementioned, in a decrease in flow velocity, but it furthermore reduces the pressure of the fluid allowing small bubbles present in the blood to expand and rise, augmenting the separating effect. As per another embodiment of the present invention, the lumen (21) of the inlet (10) is arranged with at least two segments, wherein each one of said segments has an angle of between −20° and 75° relative horizontal plane, preferably between 0° and 75°, more preferably between 35° to 55°, and most preferably approximately 45° relative a horizontal plane, in order to optimize bubble separation. Again, a horizontal arrangement, i.e. 0°, also falls within the scope of the present invention.

Figure 1:
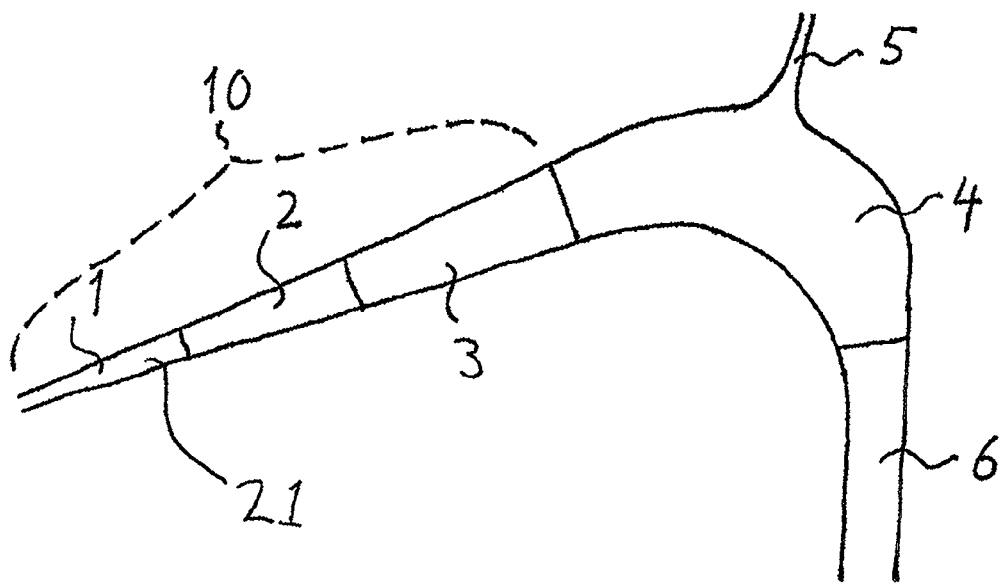
FIG. 1. Schematic exemplary illustration of one embodiment of the present invention, displaying an inlet (10) with a continuously increasing cross-sectional area.

FIG. 1 represents an embodiment of the present invention with continuously increasing cross-sectional area of the lumen (21) of the inlet (10), where the blood flow enters the microbubble reducer through segment (1) and continues upwards through segment (2) and (3). The increasing area and the inclination of the inlet relative the horizontal plane facilitate the separation of gas bubbles of all sizes. The blood is further conveyed to the curved duct means (4), where gas bubbles are removed through the gas outlet (5), before it is returned to the patient through the outlet (6). The segments in FIG. 1 are naturally primarily for illustrative purposes and shall not be considered as limiting the device, i.e. the microbubble reducer, in any way. Additionally, as per one alternative of the invention, the lumen (21) of the inlet (10) is not linear but wherein its shape can be described for instance by an exponential function or a logarithm function, or additional shapes mutatis mutandis. A lumen (21) of an inlet (10) displaying continuously increasing cross-sectional area has inherent advantages associated with aspects such as ease of manufacture and facilitated post-production modifications.

Figure 2:
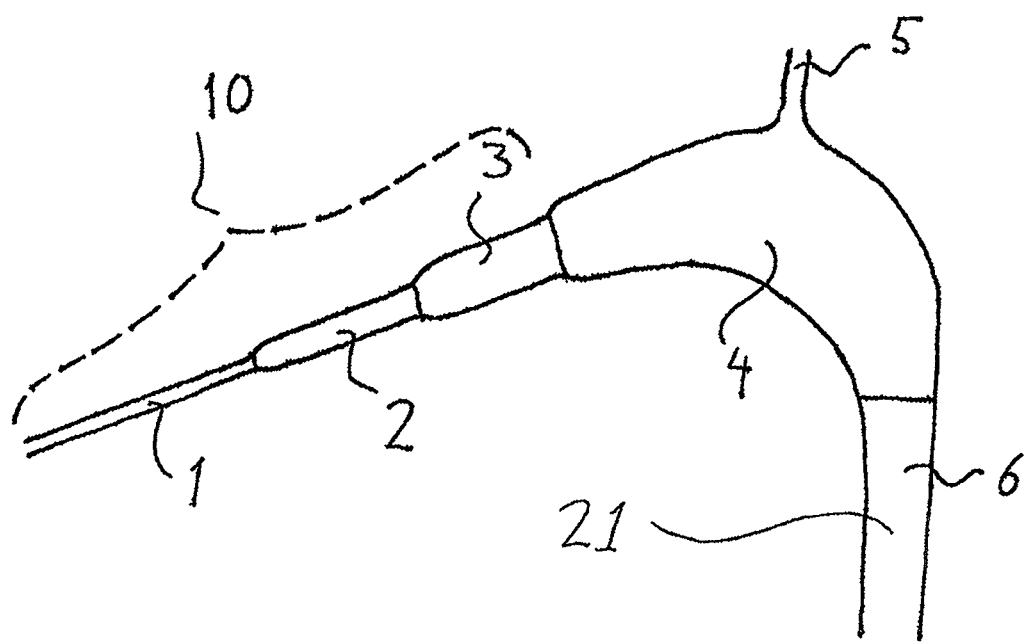
FIG. 2. Schematic exemplary illustration of one embodiment of the present invention, comprising an inlet (10) with three segments (1, 2, 3) with constant but different cross-sectional areas.

FIG. 2 represents another embodiment of the invention, where the lumen (21) of the inlet (10) is comprised of three segments with different but constant intra-segment cross-sectional areas, i. e. with the cross-sectional area of segment (1) being smaller than the cross-sectional area of segment (2), which in turn has a smaller cross-sectional area than segment (3). Thus, the non-Newtonian flow enters the device through segment (1), continues to segment (2) and segment (3) with concomitant reduction in flow velocity for optimized bubble separation, before it enters the curved duct means (4), where gas is removed through the gas outlet (5). Finally, the blood is returned to the patient through the outlet (6).

Figure 3:
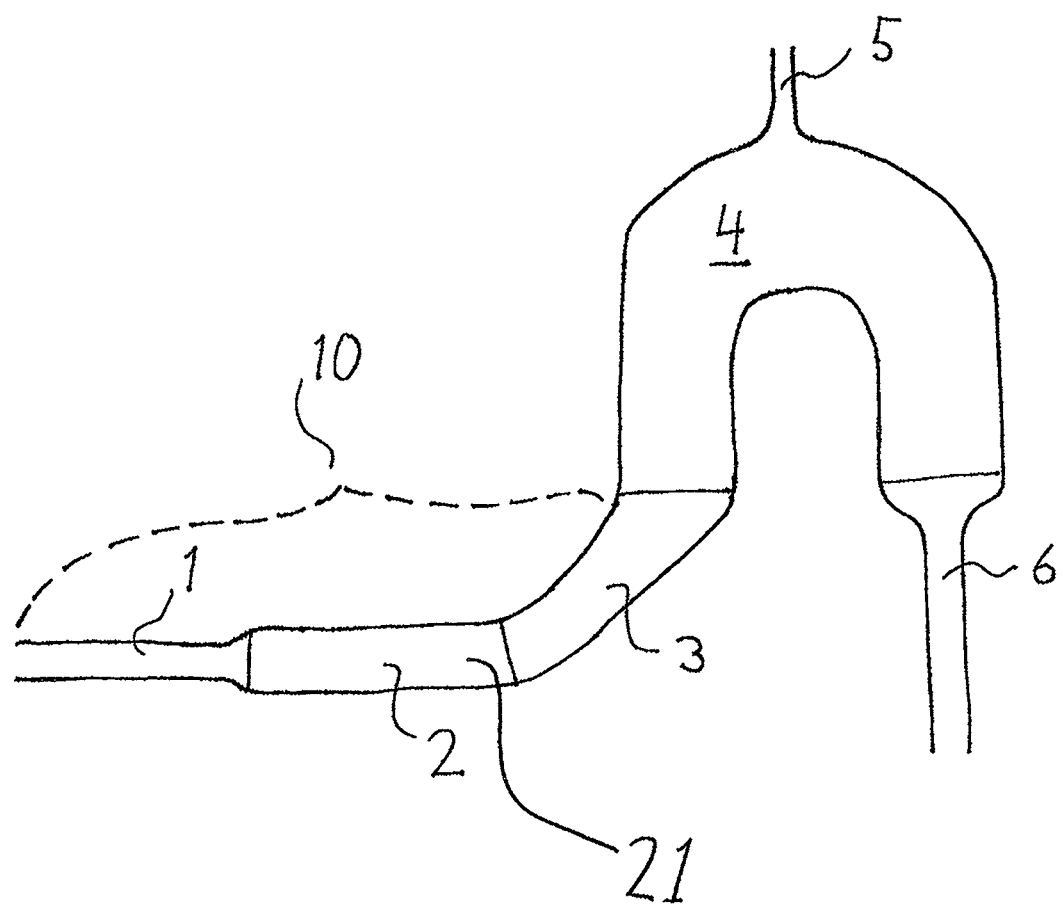
FIG. 3. Schematic exemplary illustration of one embodiment of the present invention, with an inlet (10) displaying two initial segments (1, 2) arranged horizontally and a third segment (3) arranged in an inclined fashion.

In one embodiment of the invention, represented by FIG. 3, the lumen of segment (1) and segment (2) of the inlet (10) are horizontally arranged, i. e. with an angle of 0° relative a horizontal plane, exhibiting essentially constant intra-segment cross-sectional areas, with segment (2) having a larger cross-sectional area than segment (1), in order to mediate efficient gas bubble separation. After having left segment (2), the flow rises approximately 45° through segment (3), and subsequently enters the curved duct means (4). In the present embodiment, the curved duct means (4) exhibits a shape closely resembling an inverted U, with the gas outlet (5) placed on the high point of said U shape. Finally, the blood leaves the device through the outlet (6), which is essentially perpendicularly arranged relative a horizontal plane, and continues in the venous direction.

According to another embodiment of the present invention, represented by FIG. 4, the lumen of segment (1) of the inlet (10) has a lower angle relative a horizontal plane than the remaining segments of the inlet (10), as well as a smaller cross-sectional area, in order to optimize the gas separation and removal. Whereas segment (1) has a substantially constant cross-sectional area throughout its length, segment (2), which has a steeper inclination than segment (1), exhibits an increasing intra-segment cross-sectional area, leading the non-Newtonian flow, notably blood, into segment (3), and subsequently into the curved duct means (4). The gas is removed through the gas outlet (5), before the blood flow leaves the device through the outlet (6).

Figure 5:
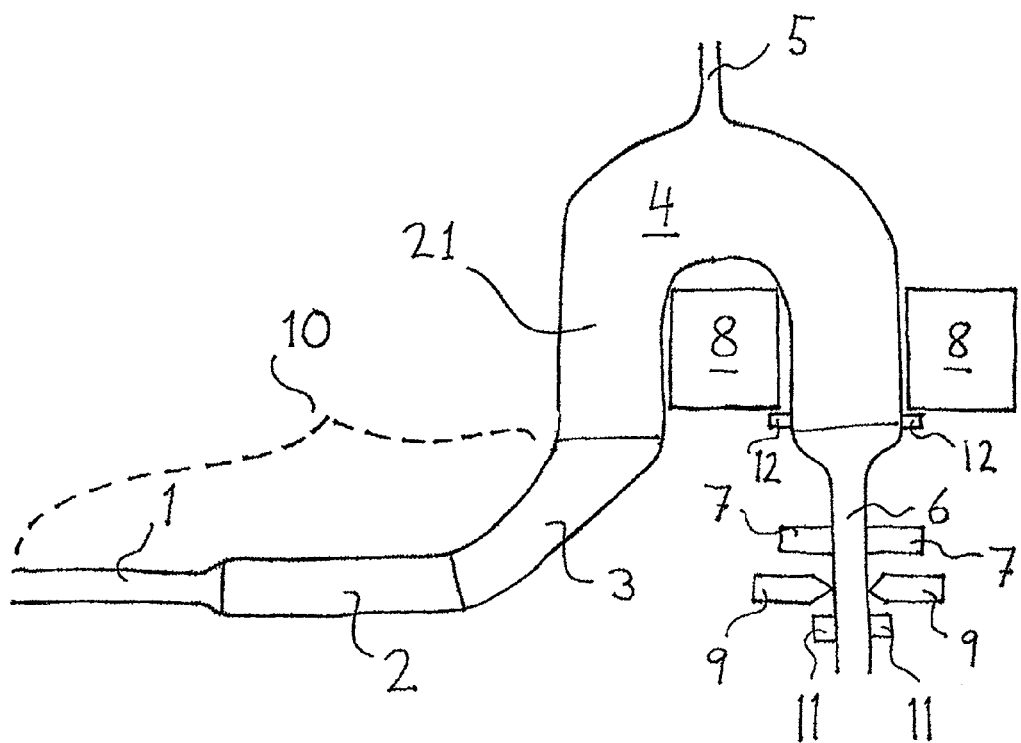
FIG. 5. Schematic exemplary illustration of one embodiment of the present invention, wherein the microbubble reducer is arranged with components commonly utilized in a dialysis setting.

In one embodiment of the invention, as represented by FIG. 5, the microbubble reducer represented by FIG. 3 is arranged together with components commonly employed in a dialysis setting. The device is arranged together with the holding means (8) of the dialysis apparatus, a venous clamp (9), and a priming detector and/or a bubble detector (7). Further, the device is equipped with additional holding means (11) and (12), in order to increase the safety of the arrangement.

All of the above-identified exemplary embodiments of the present invention allows for facile adjustment of the device, in order to enable use in conjunction with various types of dialysis machines, without the need for machine alteration or modification.

The segmented inlets (10) of certain embodiments of the present invention can optionally be manufactured individually, so as to enable individual modification and even substitution of a specific segment. However, as per another example of the invention, a segmented inlet of the device can be fabricated in one piece, for facilitated manufacture.

As per another embodiment of the present invention, the lumen (21) of the inlet (10), the curved duct means (4), the gas outlet (5), and the outlet (6) may have a cross-sectional area of between 1 mm$^2$ and 800 mm$^2$.

Further according to the invention, a first segment of the lumen (21) of the inlet (10) may have a cross-sectional area of between 1 mm$^2$ and 30 mm$^2$, preferably approximately 16 mm$^2$. Additionally according to the present invention, a second segment of the lumen (21) of the inlet (10) may display a cross-sectional area of between 1 mm$^2$ and 210 mm$^2$, preferably approximately 150 mm$^2$. In another embodiment, a third segment of the lumen (21) of the inlet (10) has a cross-sectional area of between 1 mm$^2$ and 275 mm$^2$, preferably approximately 200 mm$^2$. The purpose of the various segments relates to the shear stress the lumen/tubing exerts on the blood flow; accordingly, optimization of the cross-sectional area is critical.

As per one embodiment of the present invention, the lumen (21) of the outlet (6) may preferably have a perpendicular arrangement relative a horizontal plane, preferably with a deviation from said perpendicular arrangement with less than 80° in any direction, more preferably with less than 45° in any direction, and most preferably with less than 20° in any direction. The preferred arrangement of the outlet (6) pertains inter alia to the usage of the device, and the connections to various types of dialysis machines.

According to a further embodiment of the invention, the microbubble reducer, i.e. the lumen (21) and when relevant the lumen (41), may be substantially completely filled with non-Newtonian liquid, notably blood, during the course of operation, in order to optimize the air removal from the blood flow. In contrast to operating procedures of the devices currently in use within the art, said device does not require a gaseous zone, resulting in facilitated handling and improved gas removal. The operator is intended to use the device filled to the top, with the fluid monitored manually or by the detector at the top, in order to optimize the bubble reduction and to minimize the blood gas/air contact to prevent clotting.

According to one embodiment of the present invention, the microbubble reducer may be arranged with at least one filter. Said filter could be arranged anywhere within the device, but preferably in, or close to, the outlet (6), in order to remove potential blood clots. Further according to the invention, the device may be arranged with at least one level detector, selected from the group comprising inter alia an optical detector, an ultrasound detector, and a conductance detector, or a bubble detector on the outlet line after the device.

As per another embodiment of the invention, the curved duct means (4) or the gas outlet (5) of the device is arranged with means to enable manual fluid level detection or fluid level monitoring with the aid of a monitoring device. Said means facilitate optimized fluid level detection, further improving the handling and safety of the invention.

In yet another embodiment, the non-Newtonian fluid may be selected from the group comprising blood, blood plasma, blood substitute liquids, plasma proteins, plasma substitutes, blood substitutes, solutions of albumin and/or other plasma proteins, gelatine compositions and haemoglobin crosfumaril, as well as relatively high-viscous liquids such as dextran solutions and hydroxy ethyl starch, etc.

In one embodiment of the invention, an additional wall is arranged in the lumen (21, 41) of the device, in order to increase the shear rate at certain flows and during certain conditions, when this is desirable. Furthermore, including an additional wall may reduce the viscosity of the blood, an interesting feature for instance at low flow rates.

One aspect of the present invention relates to a method for removing gas from flow comprising non-Newtonian fluid, for instance blood. The method comprises the steps of contacting the microbubble reducer with a source of fluid/liquid, transporting the fluid through the lumen (21) of the microbubble reducer, separating any gas present in the non-Newtonian fluid, removing the gas through the gas outlet (5), and, finally, removing the blood through the outlet (6), in order to transfer it back to the patient. Additionally, in one embodiment of the invention, the gas outlet (5) may be utilized to maintain the flow level as high as possible in the upper part of the curved duct means (4).

In another aspect of the invention, an apparatus comprising the device for eliminating bubbles is connected to a dialysis machine. Additionally, another aspect of the present invention concerns the use of the device for dialysis or substantially similar treatments, obvious to a person skilled in the art, and more specifically, in one embodiment, for hemodialysis.

EXAMPLES

Materials and Methods

A prototype developed based on the present invention was compared to products currently on market, device A and device B. A standardized bubble generator was employed to generate bubbles of varying size, including microbubbles, in a solution commonly used as a blood substitute within the dialysis field. The utilized solution contains dextran and albumin and has the same viscosity as normal blood.

The solution was re-circulated from the solution-containing vessel, wherein bubbles had been produced by the bubble generator, into a dialysis tubing system of either device A or device B, or the prototype of the present invention, alternately. Bubbles present downstream of the venous chamber were detected and measured using a Hatteland Instrument (Royken, Norway), as previously described elsewhere. The measurements were performed alternately between the systems for each blood flow measured in order to reduce the risk of uneven bubble distribution and potential bubble variation.

At least ten measurements were carried out for each system at the selected flow rates (200, 300, 400, 500, and 750 ml/min), and comparative statistical analysis was carried out with non-parametrical Wilcoxon paired test.

Results

The following data was collected based on use of a dialysis system of the type shown in FIG. 3. The divergence between the two comparative tests derives from variations in exposure to microbubbles per minute between the different flow measurements.

TABLE 1

Comparison between the prototype based on the present invention and device A.

| Flow (ml/min) | Prototype (bubbles/min) | Device A (bubbles/min) | % increase | P = |
|---|---|---|---|---|
| 200 | 20.3 | 118 | 581.3 | 0.005 |
| 300 | 30.8 | 223 | 724 | 0.005 |
| 400 | 8.8 | 31.6 | 359.1 | 0.011 |
| 450 | 2.9 | | | |
| 500 | 6.7 | 121 | 1806.5 | 0.005 |
| 750 | 18.4 | 71 | 385.9 | |

TABLE 2

Comparison between the prototype based on the present invention and device B.

| Flow (ml/min) | Prototype (bubbles/min) | Device B (bubbles/min) | % increase | P = |
|---|---|---|---|---|
| 200 | 0.1667 | 0.5833 | 350 | 0.059 |
| 300 | 1.7273 | 18.5 | 1071 | 0.005 |
| 400 | 7.1 | 37.2727 | 525 | 0.005 |
| 500 | 50.8 | 349.7 | 688 | 0.005 |
| 750 | 402.2 | 1165.9 | 290 | 0.005 |

Figure 6:
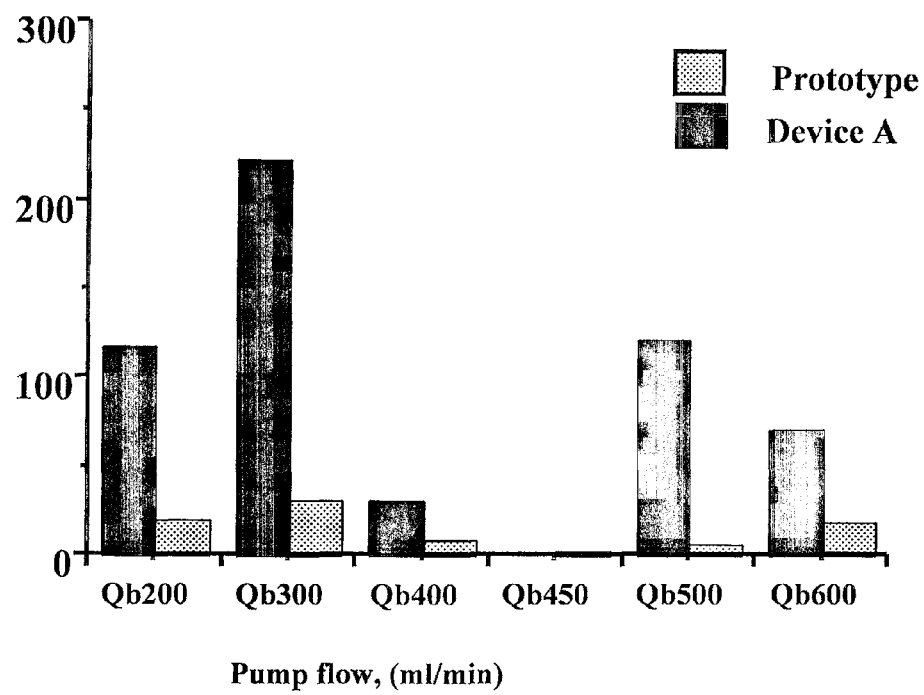
FIG. 6. Comparative graph of microbubbles/min relative various pump flows for device A and a prototype of the present invention.
Figure 7:
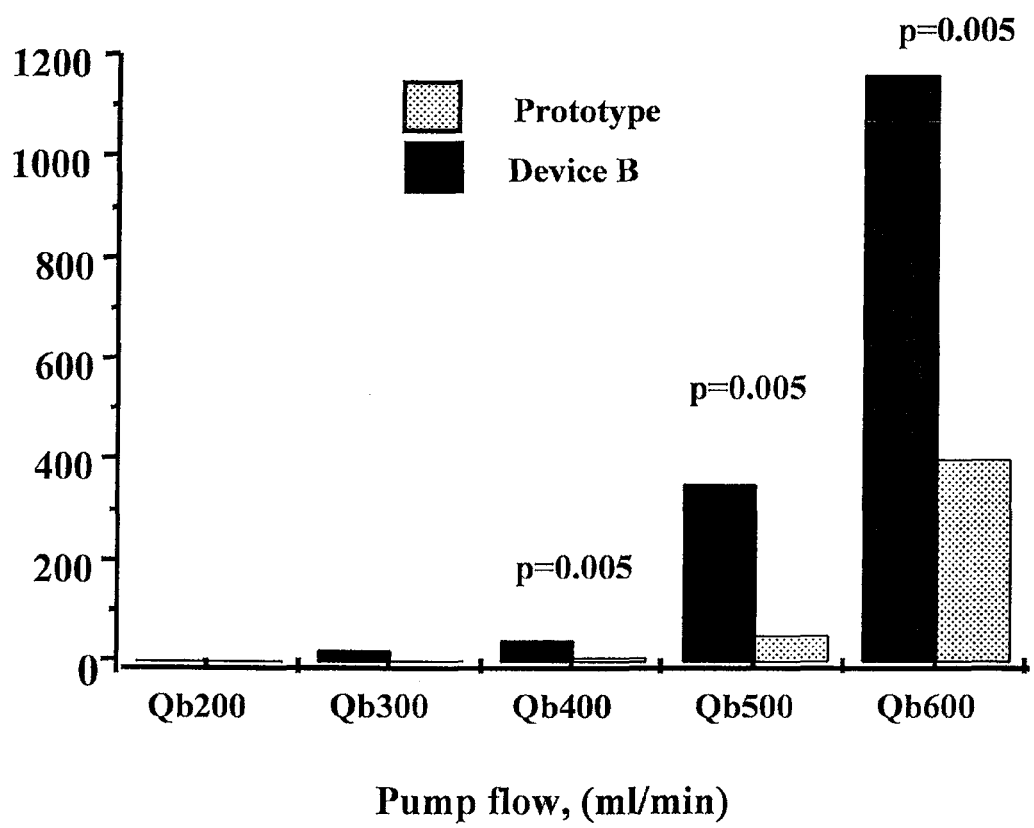
FIG. 7. Comparative graph of microbubbles/min relative various pump flows for device B and a prototype of the present invention.

As can be seen from Table 1 and Table 2, and FIG. 6 and FIG. 7, the prototype of the present invention reduced the amount of microbubbles significantly compared to the leading devices on the market today. Hence, the above results indicate the substantial advantages in terms of bubble elimination and subsequent reduction of clinical consequences when utilizing the present invention.

The invention claimed is:

1. A microbubble reducer for removing bubbles of gas from a flow comprising non-Newtonian fluid, wherein the microbubble reducer comprises:
   an inlet at a low point,
   a curved duct means comprising a gas outlet at a high point,
   an outlet at a low point, and
   a lumen that runs through said inlet, said curved duct means, said gas outlet, and said outlet,
      wherein the lumen of the inlet has an increasing cross-sectional area in the direction towards the curved duct means, and in that said lumen of the inlet is arranged with an angle of between −20° and 75° relative a horizontal plane wherein the lumen of the inlet has a length of at least 2 cm.

2. The microbubble reducer according to claim 1, wherein the running of the lumen through said inlet, through said curved duct means, through said gas outlet, and through said outlet can be described by at least one continuous function without singularities.

3. The microbubble reducer according to claim 1, wherein the curved duct means is in the form of a substantially inverted U.

4. The microbubble reducer according to claim 1, further comprising an extension channel comprising a lumen, wherein said extension channel is arranged so that the lumen empties into the lumen of the inlet, wherein said extension channel has a length of at least 2 cm.

5. The microbubble reducer according to claim 4, wherein the extension channel is arranged with an angle of between −20° and 75° relative a horizontal plane.

6. The microbubble reducer according to claim 1, wherein the distance from the start of inlet to the highest point of the lumen of the curved duct means is at least 3 cm.

7. The microbubble reducer according to claim 1, wherein the lumen of the inlet is horizontally arranged or is arranged with an angle of between 0° and 75° relative a horizontal plane.

8. The microbubble reducer according to claim 1, wherein the lumen of the inlet is divided into at least two segments, wherein each one of said segments is arranged with an angle of between 0° and 75° relative a horizontal plane.

9. The microbubble reducer according to claim 8, wherein the lumen of a first segment of the inlet has a cross-sectional area of between 1 mm$^2$ and 30 mm$^2$.

10. The microbubble reducer according to claim 8, wherein the lumen of a second segment of the inlet has a cross-sectional area of between 1 mm$^2$ and 210 mm$^2$.

11. The microbubble reducer according to claim 8, wherein the lumen of a third segment of the inlet has a cross-sectional area of between 1 mm$^2$ and 275 mm$^2$.

12. The microbubble reducer according to claim 1, wherein the lumen of the inlet, of the curved duct means, of the gas outlet, and of the outlet has a cross-sectional area of between approximately 1 mm$^2$ and 800 mm$^2$.

13. The microbubble reducer according to claim 1, wherein the lumen of the outlet has a perpendicular arrangement relative a horizontal plane.

14. The microbubble reducer according to claim 1, wherein the microbubble reducer is arranged with at least one filter.

15. The microbubble reducer according to claim 1, wherein the microbubble reducer is arranged with at least one level detector, selected from the group comprising an optical detector, an ultrasound detector, and a conductance detector, or a bubble detector placed on the outlet.

16. The microbubble reducer according to claim 1, wherein the curved duct means or the gas outlet are arranged so as to enable manual or automatic detection of the fluid level.

17. An apparatus comprising the microbubble reducer according to claim 1, wherein the microbubble reducer is connected to a dialysis machine.

18. A method for removing gas from a flow comprising non-Newtonian fluid, comprising:
    connecting a microbubble reducer according to claim 1 to a source of non-Newtonian fluid;
    transporting the fluid through the lumen of said microbubble reducer;
    removing the gas through a gas outlet of the micro bubble reducer; and
    removing fluid through an outlet of the microbubble reducer.

19. The method according to claim 18 wherein the gas outlet is utilized to maintain the flow comprising non-Newtonian fluid as high as possible in the upper part of the curved duct means.

* * * * *